US009423379B2

(12) United States Patent  
Cordeiro et al.

(10) Patent No.: US 9,423,379 B2  
(45) Date of Patent: Aug. 23, 2016

(54) MEASUREMENT OF SLURRY DENSITY

(75) Inventors: Luiz Alberto Cordeiro, Western Australia (AU); Maxim Lebedev, Western Australia (AU); Boris Gurevich, Western Australia (AU)

(73) Assignees: Total Marine Technology Pty Ltd, Bibra Lake, Western Australia (AU); Curtin University of Technology, Bentley, Western Australia (AU)

( * ) Notice: Subject to any disclaimer, the term of this patent is extended or adjusted under 35 U.S.C. 154(b) by 776 days.

(21) Appl. No.: 13/806,245

(22) PCT Filed: Jun. 28, 2011

(86) PCT No.: PCT/AU2011/000795  
§ 371 (c)(1),  
(2), (4) Date: Mar. 4, 2013

(87) PCT Pub. No.: WO2012/000027  
PCT Pub. Date: Jan. 5, 2012

(65) Prior Publication Data  
US 2013/0145843 A1 Jun. 13, 2013

(30) Foreign Application Priority Data  
Jun. 28, 2010 (AU) .................. 2010902837

(51) Int. Cl.  
*G01N 29/028* (2006.01)  
*G01N 9/36* (2006.01)  
*E21B 47/00* (2012.01)  
(Continued)

(52) U.S. Cl.  
CPC .......... *G01N 29/028* (2013.01); *E21B 47/0005* (2013.01); *G01N 9/24* (2013.01); *G01N 9/36* (2013.01); *G01N 29/032* (2013.01); *G01N 2291/011* (2013.01);  
(Continued)

(58) Field of Classification Search  
CPC ......... C08L 5/00; A61L 24/08; A61L 31/042; A61L 24/0042; A61L 31/148; E21B 47/101; F04C 19/001; G01H 15/00; G01H 5/00; G01N 2291/02818; G01N 29/024  
USPC .................................. 73/24, 32, 152; 702/54  
See application file for complete search history.

(56) References Cited

U.S. PATENT DOCUMENTS

| 4,571,693 A | 2/1986 | Birchak et al. ................. 364/509 |
| 4,631,410 A * | 12/1986 | Nickles ..................... G01T 1/20 250/207 |

(Continued)

FOREIGN PATENT DOCUMENTS

| AU | WO 2012000027 A1 * | 1/2012 | .......... E21B 47/0005 |
| GB | 2 181 243 | 4/1987 | ............. G01H 11/06 |
| WO | WO 03/078996 | 9/2003 | ............. G01N 29/02 |

OTHER PUBLICATIONS

Judith A., Measuring fluid and slurry density and solids concentration non-invasively,2004,Pacific Northwest National Laboratory, pp. 563-567.*

(Continued)

Primary Examiner — Hezron E Williams  
Assistant Examiner — Gedeon M Kidanu  
(74) Attorney, Agent, or Firm — Kusner & Jaffe

(57) ABSTRACT

A method for determining the density of cement slurry in undersea drilling is disclosed. The method uses the reflection of acoustic waves from the slurry in order to determine its acoustic impedance and thus its density.

8 Claims, 1 Drawing Sheet

(51) Int. Cl.
*G01N 9/24* (2006.01)
*G01N 29/032* (2006.01)

(52) U.S. Cl.
CPC ............... *G01N 2291/02416* (2013.01); *G01N 2291/02818* (2013.01); *G01N 2291/044* (2013.01)

(56) References Cited

U.S. PATENT DOCUMENTS

| | | | | |
|---|---|---|---|---|
| 6,050,141 | A * | 4/2000 | Tello | E21B 21/08 73/152.56 |
| 6,913,079 | B2 * | 7/2005 | Tubel | E21B 47/00 114/382 |
| 2005/0215902 | A1 * | 9/2005 | Greenwood | G01N 29/07 600/446 |
| 2007/0144240 | A1 * | 6/2007 | Andle | G01N 9/24 73/32 A |
| 2009/0266165 | A1 * | 10/2009 | Greenwood | G01N 29/024 73/597 |
| 2013/0058193 | A1 * | 3/2013 | Roberts | G01V 1/44 367/35 |

OTHER PUBLICATIONS

Bamberger, J.A. et al.; "Measuring fluid and slurry density and solids concentration non-invasively," Ultrasonics vol. 42 (2004); Abstract—2 pages.

VanDeventer, J. et al.; "An ultrasonic density probe," (1997); Ultrasonics Symposium, 1997 Proceedings, 1997 IEEE; Abstract—1 page.

Form PCT/ISA/210—Int'l Search Report (from corresponding Int'l Patent App. No. PCT/AU2011/000795—3 pages.

* cited by examiner

MEASUREMENT OF SLURRY DENSITY

FIELD OF THE INVENTION

The present invention relates to a method of measuring the density of cement slurry. It has particular application in the underwater drilling industry, where a cement slurry may be pumped a considerable distance from, for instance, a surface vessel to an under-water location. The invention has been conceived in relation to grouting of offshore platform legs, but has wider application.

BACKGROUND TO THE INVENTION

Accurate measurement of cement slurry density has long been a problem where the slurry is being pumped over some distance. At source, the density can be calculated by weighing a known volume, but where the slurry is then subjected to compression and acceleration by pumps, and/or supplied to an area of different ambient pressure, the density at destination is often only approximated relative to density at the source.

This is particularly problematic in undersea operations, such as in the grouting of oil/gas platforms to the seabed. Such operations often require the pumping of cement slurry to the sea bed, typically in depths of hundreds of meters, and indeed to locations at least tens of meters below the seabed.

Knowledge of the slurry density at these depths allows calculation of the required slurry volume. This, in turn, can provide an indication of the integrity of the grout around a platform leg. Approximations of density calculated from the surface are simply not sufficiently accurate to provide this indication.

In order to provide a more accurate measurement of slurry density at the destination, it is known to use a remote nuclear-source densimeter. A nuclear-source densimeter uses a radio-active source of gamma rays such as caesium or americium. These are directed through the slurry to a detector, which calculates density based on the attenuation of the gamma rays.

The use of nuclear-source densimeters can be problematic. In particular, they can expose workers to gamma rays, presenting safety risks. Additionally, they can be expensive, and difficult to recover from an undersea cement pouring or grouting operation.

Other techniques for determining cement density have been used. In particular, coriolis flow meters are often used. These too are problematic as they require cement to be forced through narrow tubes in order for its density to be calculated.

Other techniques attempted include the use of strain gauges attached to tubes in an attempt to determine the weight of the tube. As with coriolis flow meters, this requires the forcing of cement through narrow tubes. The measuring of differential pressures has also been attempted, however this has proved impractical.

All of the techniques discussed share a further limitation, in that they can only measure density of a cement slurry within a pipe. Although knowledge of the slurry density as it exits a pipe below the sea bed is useful, it leaves open the possibility that due to cavities (caves) beneath the sea bed, and mixing of the slurry with mud, the actual density of the slurry in situ is significantly different to that of the slurry exiting the pipe.

The present invention arose from the realisation that density could be measured by the acoustic impedance of a slurry to ultrasonic waves. Attempts were made to measure this impedance by passing a wave through the slurry to a receiver. These attempts proved fruitless, as the heterogeneous nature of a cement slurry and the presence of so many suspended particles resulted in scattering of the waves and quick attenuation. Further research was conducted in order to arrive at the present invention.

SUMMARY OF THE INVENTION

The present invention is based on the principle that when acoustic waves impact a boundary between two media, some of the wave energy will be reflected. The amount of wave energy reflected can be predicted by knowledge of the respective impedances of the two media.

According to one aspect of the present invention there is provided a method of determining the density of a cement slurry, the method including the steps of providing a conducting unit of known acoustic impedance, the conducting unit having a first side and a second side which are opposite each other; locating the conducting unit such that the second side is in contact with the cement slurry; providing an incident acoustic wave of known amplitude to the first side of the conducting unit; measuring the amplitude of a reflected wave at the first side of the conducting unit; calculating the acoustic impedance of the slurry based on the respective amplitudes of the incident and reflected waves; and calculating the density of the slurry based on its acoustic impedance.

The method may include the additional step of measuring the acoustic wave velocity in the cement slurry.

According to a second aspect of the present invention there is provided a method of determining the density of a cement slurry beneath a sea bed, the method including the steps of pumping a cement slurry from a supply pipe into a cavity beneath the sea bed; providing a conducting unit of known acoustic impedance within the cavity, the conducting unit having a first side and a second side which are opposite each other; locating the conducting unit such that the second side is in contact with the cement slurry; providing an incident acoustic wave of known amplitude to the first side of the conducting unit; measuring the amplitude of a reflected wave at the first side of the conducting unit; calculating the acoustic impedance of the slurry based on the respective amplitudes of the incident and reflected waves; and calculating the density of the slurry based on its acoustic impedance.

It is preferred that the conducting unit be moveable relative to the cavity, such that the conducting unit may be moved in conjunction with the supply of slurry into the cavity, in order to determine slurry density throughout the cavity.

In accordance with a third aspect of the present invention there is provided a method of indicating completion of an undersea cement pouring by determining the density of sea water near the cement pouring, the method including the steps of pumping a cement slurry from a supply pipe into a cavity beneath the sea bed; providing a conducting unit of known acoustic impedance above the sea bed near the cavity, the conducting unit having a first side and a second side which are opposite each other; providing a series of incident acoustic waves of known amplitude to the first side of the conducting unit; measuring the amplitude of reflected waves at the first side of the conducting unit; calculating the acoustic impedance of the sea environment based on the respective amplitudes of the incident and reflected waves; calculating the density of the sea water environment based on its acoustic impedance; and monitoring the measurements to determine when the density of the sea environment approaches that of the cement slurry.

It will be appreciated that the calculation steps may be combined into a single calculation.

It is preferred that the incident acoustic wave be an ultrasonic wave. It is considered that acoustic waves having frequency in the range 250 kHz to 2.0 MHz may be particularly suited to this application.

It is also preferred that amplitude of the reflected wave be determined with respect to an early waveform peak of the reflected wave, such as an initial waveform peak or a second waveform peak.

According to a fourth aspect of the present invention there is provided an apparatus for measuring the density of a cement slurry, the apparatus including an acoustic wave generator, an acoustic wave detector, and a conducting unit having a first side and a second side which are opposite each other, the acoustic wave generator being located on the first side of the conducting unit and being arranged to send acoustic waves through the conducting unit towards the second side, and the acoustic wave detector being located on the first side of the conducting unit and being arranged to determine the amplitude of acoustic waves reflected from the second side of the conducting unit.

The acoustic wave generator and acoustic wave detector may be housed within a single unit. In a preferred embodiment of the invention, the generator and the detector may be supplied as a piezoelectric transmitter/receiver.

The conducting unit may be formed from a suitable plastic material, such as poly(methyl methacrylate) (Perspex™).

The calculations performed to determine slurry density are based on the formula:

$$\frac{A_{reflected}}{A_0} = \frac{Z_1 - Z_2}{Z_1 + Z_2}$$

where $A_0$ is the amplitude of the incident wave; $A_{reflected}$ is the amplitude of the reflected wave; $Z_1$ is the acoustic impedance of the first medium (the conducting unit); and $Z_2$ is the acoustic impedance of the second medium (the slurry).

The acoustic impedance can be calculated as $$Z = \rho \cdot v$$

Where Z is the acoustic impedance; $\rho$ is the density; and v is the acoustic wave velocity (the speed of sound) in the medium.

It will be appreciated that the speed of sound within the slurry will vary according to the properties of the particular slurry being employed, and hence calibration of the sensor is required before deployment.

DESCRIPTION OF PREFERRED EMBODIMENTS

The present invention can be deployed in many different environments. It will be convenient to further describe the invention with reference to particular embodiments of the present invention, and situations in which it can be used. Other embodiments are possible, and consequently the particularity of the following discussion is not to be understood as superseding the generality of the preceding description of the invention.

Grouting of Platform Legs

The present invention can be utilised in the grouting of legs of offshore platforms, such as oil/gas platforms. In this application, a sensor is placed outside the leg being grouted, within the cavity being filled with grout. The sensor is initially located towards a bottom of the cavity, near where grout is to be initially supplied.

As grout is supplied into the cavity, the sensor is arranged to calculate the density of this grout around the platform leg. In particular, it can be used to indicate whether the grout is consistent at the sensor's location, or whether there is too much mud and water mixing with the grout.

When the grout at the location has a desired density, indicating the completion of that part of the grouting, the sensor can be drawn upwards along with the grout supply pipe head. Continuous monitoring of the slurry density around the sensor will indicate the next location where more grout is required.

This process can continue until the sensor reaches the seabed, thus providing a high degree of confidence in the grouting of the platform leg.

Monitoring of Well Casing Cementing

The cementing into position of an initial well casing is an important operation, and presents many difficulties. One difficulty is in knowing when sufficient cement slurry has been supplied around the casing. Traditionally, this has required a submersible vehicle to be located near the casing being cemented into position, so that operators can visually determine when cement slurry begins to spill from the cavity around the casing.

Visual assessment of this is problematic, as the cementing operation involves displacing mud located within the cavity. The expulsion of the mud from the cavity into the sea water means that visibility is extremely poor.

It is proposed to use a sensor tool of the present invention, located above the sea floor in the vicinity of the cavity, in order to overcome this problem. Monitoring of the ambient density will provide a clear indication of cement slurry reaching the sea floor.

Bench Scale Tests

Figure 1:
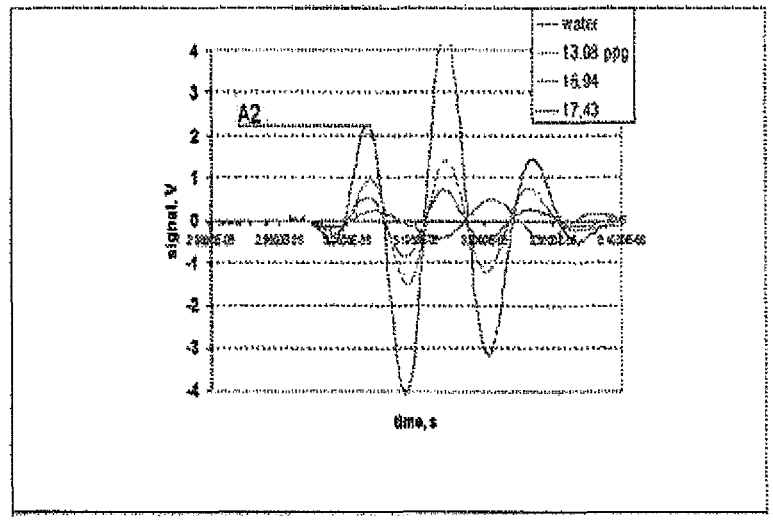
FIG. 1 is a graphical view illustrating an example of test results obtained using an apparatus for measuring density of a cement slurry.

In example bench-scale tests, the data illustrated in FIG. 1 was obtained using a conducting unit formed of 40 mm poly (methyl methacrylate), having a density of 9.93 ppg and using three different slurries of known density in addition to water (density 8.33 ppg).

The second peak (marked A2) is considered the most preferable on which to base measurements.

Figure 2:
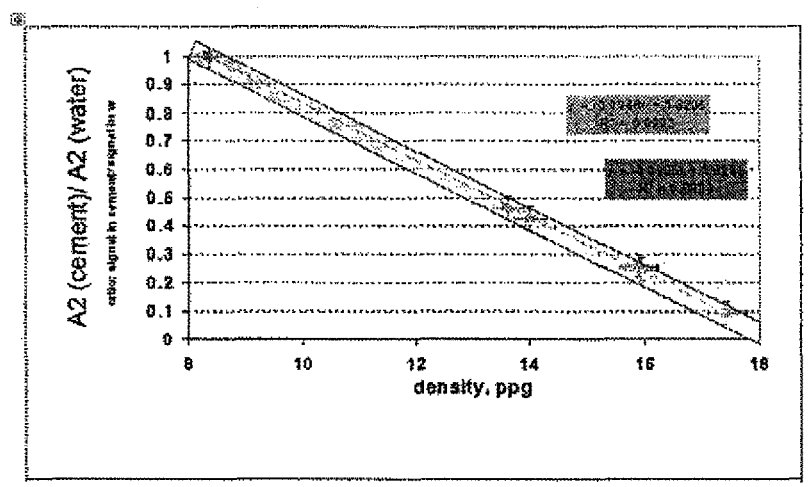
FIG. 2 is a graphical view illustrating a further example of test results obtained using an apparatus for measuring density of a cement slurry.

Further example tests, as illustrated in FIG. 2, were conducted using two independent ultrasonic sensors, over a range of slurries of different densities. The results plotted show the ratio of $A_{reflected}$ for each slurry to $A_{reflected}$ for water. These measurements were taken at 25° C.±2° C.

The results demonstrate a strong correlation between the measured reflected amplitude and slurry density.

Modifications and variations as would be apparent to a skilled addressee are deemed to be within the scope of the present invention.

The invention claimed is:

1. A method of determining a density of a cement slurry beneath a sea bed, the method including the steps of:
   pumping a cement slurry from a supply pipe into a cavity beneath the sea bed;

providing a conducting unit of known acoustic impedance within the cavity, the conducting unit having a first side and a second side which are opposite each other;

locating the conducting unit such that the second side is in contact with the cement slurry;

moving the conducting unit relative to the cavity in conjunction with the pumping of the cement slurry into the cavity;

providing an incident acoustic wave of known amplitude to the first side of the conducting unit;

measuring an amplitude of a reflected wave at the first side of the conducting unit;

calculating the acoustic impedance of the cement slurry based on the respective amplitudes of the incident and reflected waves; and calculating a density of the cement slurry based on the acoustic impedance of the cement slurry.

2. A method of determining the density of a cement slurry beneath a sea bed as claimed in claim 1, wherein the amplitude of the reflected wave is determined with respect to an initial waveform peak or a second wave waveform peak.

3. A method of determining the density of a cement slurry beneath a sea bed as claimed in claim 1, wherein the incident acoustic wave is an ultrasonic wave.

4. A method of determining the density of a cement slurry beneath a sea bed as claimed in claim 3, wherein the ultrasonic wave has a frequency in a range of 250 kHz to 2.0 MHz.

5. A method of indicating completion of an undersea cement pouring by determining a density of a sea water environment near the cement pouring, the method including the steps of:

pumping a cement slurry from a supply pipe into a cavity beneath the sea bed;

providing a conducting unit of known acoustic impedance above the sea bed near the cavity, the conducting unit having a first side and a second side which are opposite each other;

moving the conducting unit relative to the cavity in conjunction with the pumping of the cement slurry into the cavity;

providing a series of incident acoustic waves of known amplitude to the first side of the conducting unit;

measuring an amplitude of reflected waves at the first side of the conducting unit;

calculating an acoustic impedance of the sea water environment based on the respective amplitudes of the incident and reflected waves;

calculating the density of the sea water environment based on the acoustic impedance of the sea water environment; and monitoring the measurements to determine when the density of the sea water environment approaches the density of the cement slurry.

6. A method of indicating completion of an undersea cement pouring as claimed in claim 5, wherein the amplitude of the reflected waves is determined with respect to an initial waveform peak or a second wave waveform peak.

7. A method of indicating completion of an undersea cement pouring as claimed in claim 5, wherein the incident acoustic wave is an ultrasonic wave.

8. A method of indicating completion of an undersea cement pouring as claimed in claim 7, wherein the ultrasonic wave has a frequency in a range of 250 kHz to 2.0 MHz.

* * * * *